United States Patent [19]

Ishihara et al.

[11] Patent Number: 4,974,725
[45] Date of Patent: Dec. 4, 1990

[54] CONTAINER FOR ORGANOLEPTICALLY ACTIVE SUBSTANCE

[76] Inventors: Yoshiko Ishihara, 8-7, Mori Minami 1-chome, Higashinadaku, Kobe, Japan; Yukio Kawanishi, 1-22, Hachizuka 1-chome, Ikedashi, Osaka, Japan

[21] Appl. No.: 485,198

[22] Filed: Feb. 26, 1990

[30] Foreign Application Priority Data

Mar. 3, 1989 [JP] Japan ............................... 1-24955[U]

[51] Int. Cl.$^5$ ......................... A61L 9/04; B65D 81/26
[52] U.S. Cl. .................................... 206/0.5; 206/219; 206/524.7; 422/5
[58] Field of Search ............. 206/0.5, 219, 221, 484.1, 206/568, 524.7, 524.1; 436/1, 166, 178; 422/1, 5, 29

[56] References Cited

U.S. PATENT DOCUMENTS

| | | | |
|---|---|---|---|
| 3,294,224 | 12/1966 | Horwitz | 206/0.5 |
| 3,946,945 | 3/1976 | Odioso et al. | 206/0.5 X |
| 4,340,491 | 7/1982 | Lee | 206/0.5 X |
| 4,374,571 | 2/1983 | Hirvela | 206/0.5 X |
| 4,511,552 | 4/1985 | Cox | 422/5 |
| 4,634,614 | 1/1987 | Holzner | 206/484.1 X |
| 4,749,600 | 6/1988 | Cullen et al. | 206/524.7 X |

Primary Examiner—Paul T. Sewell
Assistant Examiner—Jacob K. Ackun, Jr.
Attorney, Agent, or Firm—Jordan and Hamburg

[57] ABSTRACT

An organoleptically active substance container for producing a deodorant, scenting and/or repellent effect comprises an envelope made of water-impermeable, gas-permeable synthetic resin in which a mixture of an organoleptically active substance in powder form, typically a deodorant, perfume or repellent, and a powdery water-absorbing synthetic resin is contained either as such or packed in a water-soluble film, the envelope being equipped, at one corner thereof, with a tightly closable water inlet for introducing water into the envelope.

With the above container, a simple procedure comprising only introducing water into the water-impermeable, gas-permeable synthetic resin envelope makes it possible to secure the desired deodorant, scenting and/or repellent effect, among others, for a prolonged period of time. Since the powdery water-absorbing synthetic resin powder-active substance powder mixture is placed, either as such or in the form of a pack, in the envelope, the container as a whole is not bulky but lightweight before use, hence can be stored in transported with ease.

4 Claims, 1 Drawing Sheet

CONTAINER FOR ORGANOLEPTICALLY ACTIVE SUBSTANCE

BACKGROUND OF THE INVENTION a. Technical Field of the Invention

This invention relates to a container containing an organoleptically active substance capable of producing a deodorant, scenting and/or insect repellent effect. Such container is to be positioned at places where said effect is to be produced, for example in a room, car, toilet room and refrigerator.

b. Prior Art

Various containers containing such organoleptically active substances as deodorants, perfumes and insect repellents are known. While they are designed so that the effects of such substances may be produced for a prolonged period of time, the duration of the effects is not satisfactorily long as yet. Furthermore, the known containers of this kind cause inconveniences: they are bulky and require much space for transportation and storage before use.

OBJECT OF THE INVENTION

Having been accomplished to solve the above problems encountered with the conventional containers for organoleptically active substance, the present invention has as its object to provide an organoleptically active substance container which allows the deodorant, scenting and/or repellent effect to last for a prolonged period of time and which is less bulky before use and can be stored and transported conveniently.

SUMMARY OF THE INVENTION

The organoleptically active substance container according to the invention is characterized in that it comprises an envelope made of a synthetic resin impermeable to water but permeable to gases in which envelope a mixture of at least one organoleptically active substance in powder form and a water-absorbing synthetic resin in powder form is contained either as such or packed in an inner bag or pouch made of a water-soluble synthetic resin film, and in that the envelope has, at one corner thereof, a tightly closable water inlet for introducing water into said envelope.

The term "organoleptically active substance in powder form" as used herein means that the substance itself occurs as a powder or that the substance is borne on a water-insoluble granular carrier. Said active substance includes deodorants, perfumes, insect repellents and the like.

In the organoleptically active substance container according to the invention, introduction of water into the envelope made of a water-impermeable, gas-permeable synthetic resin results in absorption of water by the water-absorbing synthetic resin. the latter resin swells to give a jelly-like substance, which fills the envelope. On the occasion of water absorption by the water-absorbing synthetic resin, the deodorant, perfume, repellent or the like contained in powder form in the mixture thereof with the water-soluble synthetic resin powder is taken up by and entrapped in the swollen water-absorbing synethetic resin gel and maintained there stably.

When the powder mixture is contained in the inner bag or pouch, the water introduced into the water-impermeable, gas-permeable synthetic resin envelope dissolves the water-soluble synthetic resin bag or pouch packing up the powder mixture, whereby the water-absorbing synthetic resin in said bag or pouch absorbs water and swells to give a gel-like matter, which fills the envelope. On the occasion of water absorption by the water-absorbing synthetic resin, the powdery deodorant, perfume, insect repellent or the like contained in the bag or pouch is taken up by and entrapped in the swollen water-absorbing synthetic resin gel and maintained therein stably.

Thus, when the organoleptically active substance entrapped in the resin gel is a deodorant, the deodorant permeates the gas-permeable synthetic resin envelope and is gradually released into the ambient atmosphere, the rate of release depending on the gas permeability of the gas-permeable synthetic resin envelope and/or the moisture-releasing property of the water-absorbing synthetic resin. When the active substance is a perfume or a repellent, the substance permeates the gas-permeable synthetic resin envelope owing to its own diffusibility and volatility and is released into the atmosphere. In this way, the desired deodorant, scenting, repellent or the like effect is secured for a prolonged period of time.

The organoleptically active substance container according to the invention requires only a simple procedure comprising introducing water into the water-impermeable, gas-permeable synthetic resin envelope for producing a long-lasting deodorant, scenting, repellent or similar effect as desired. Furthermore, since the organoleptically active substance container according to the invention comprises an envelope in which a mixture of a water-absorbing synthetic resin powder and an organoleptically active substance powder is contained either as such or packed in an inner bag or pouch, the container as a whole is not bulky but lightweight before use, so that it is convenient for its storage and transportation.

DETAILED DESCRIPTION OF PREFERRED EMBODIMENTS

Figure 1:
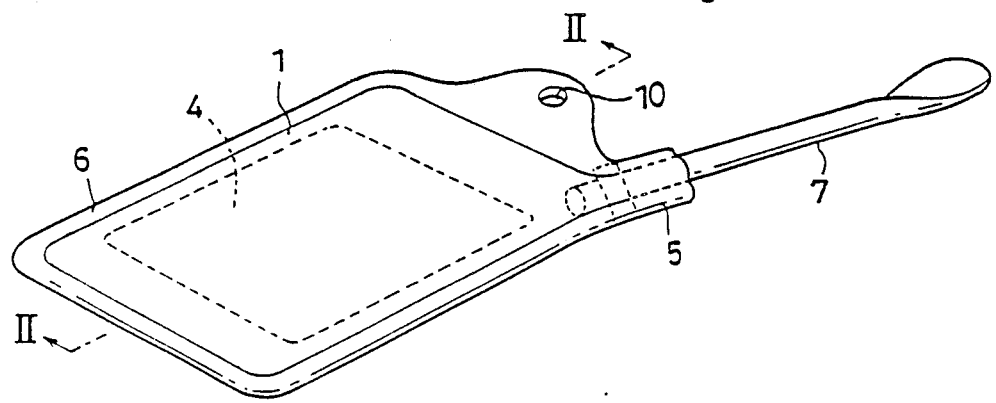
FIG. 1 is a perspective view showing an embodiment of the organoleptically active substance container according to the invention.

Preferred examples of the organoleptically active substance container according to the invention will be described hereinbelow with reference to the drawing.

Figure 2:
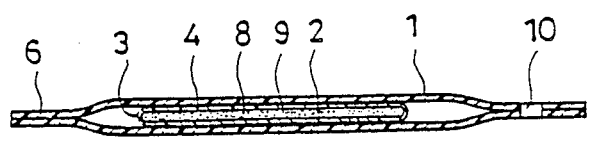
FIG. 2 is a sectional view showing the same container as seen along the line II—II shown in FIG. 1.

As shown in FIG. 1 and FIG. 2, the organoleptically active substance container according to the invention comprises an envelope 1 made of a water-impermeable, gas-permeable synthetic resin and an organoleptically active substance pack 4 comprising a water-soluble film 3 and a powder mixture 2 wrapped up in the film and composed of an organoleptically active substance powder 9 and a water-absorbing synthetic resin powder 8. The envelope 1 has, at one corner thereof, a tightly closable water inlet 5 for introducing water into the envelope 1. The whole periphery of the envelope 1 is tightly sealed by means of a heat-sealed portion 6, for instance, except for the part associated with the water inlet 5 mentioned above.

The water inlet 5 may be constituted, for example, such that insertion of a tubular water inlet means 7 (e.g. straw) into it enables introduction of water into the envelope 1 and that removal of the means 7 from the water inlet 5 following water introduction can result in tight closure of the envelope 1. Commercially available means, for instance, may be used in constructing the water inlet 5.

As particularly shown in FIG. 2, the active substance pack 4 comprises a bag or pouch made of a water-soluble synthetic resin film, for example a polyvinyl alcohol film, and filled with a mixture 2 of a water-absorbing synthetic resin powder 8, for example a polyacrylic acid powder, and an organoleptically active substance powder 9. The powdery deodorant is not limited to any particular species buy may be a porous substance, for example coral having deodorant activity. A perfume or repellent may be borne on such porous substance or some other known porous substance as a carrier therefor.

The water-impermeable, gas-permeable synthetic resin envelope 1 is preferably made of a fluororesin, and a hot-melt synthetic resin film should preferably be laminated to the envelope at least in the heat seal portion mentioned above in an appropriate manner. The water-impermeable, gas-permeable synthetic resin envelope 1 may also be produced by using a sheet or the like made by molding a mixture of polyethylene and calcium carbonate or barium carbonate. The material for envelope preparation is not limited to any particluar species.

The envelope 1 may have an appropriate tunglike elongation with a perforation 10 therewithin, which may serve as a means of attaching the envelope to a desired site or place.

Figure 3:
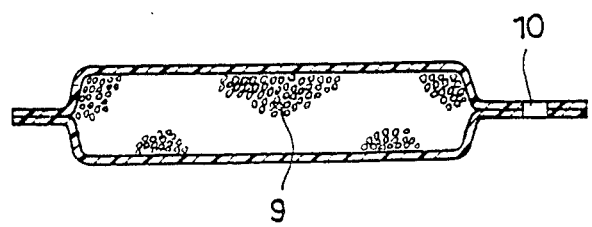
FIG. 3 is a sectional view showing the container as brought about after introduction of water into the envelope.

In the organoleptically active substance container according to the invention, introduction of water into the water-impermeable, gas-permeable synthetic resin envelope 1 through the water inlet 5 causes dissolution of the water-soluble film 3, as shown in FIG. 3, whereby the powdery water-absorbing synthetic resin 8 absorbs water, swells and becomes jelly-like, forming a gel. The active substance 9 is taken up by and entrapped in the thus-swollen water-absorbing synthetic resin. Polyacrylic acid, one of the typical water-absorbing synthetic resins, is generally capable of absorbing 200 to 300 weights of water and the water once absorbed thereby can hardly be released therefrom. When such an absorbent resin is used in the container according to the invention, the deodorant, scenting, repellent and/or the like effect can be secured for a prolonged period of time.

What is claimed is:

1. An organoleptically active substance container which comprises an envelope made of a water-impermeable, gas-permeable synthetic resin, a powder mixture contained in the envelope and composed of an organoleptically active substance in powder form and a water-absorbing synthetic resin in powder form, and a water inlet positioned at one corner of the envelope for introducing water into the envelope.

2. An organoleptically active substance container as claimed in claim 1, wherein the powder mixture is wrapped up or packed in a water-soluble film and the resultant pack is placed in the water-impermeable, gas-permeable synthetic resin envelope.

3. An organoleptically active substance container as claimed in claim 1, wherein the powdery active substance is borne on a granular carrier.

4. An organoleptically active substance container as claimed in claim 1, wherein the powdery active substance is at least one member of the class consisting of deodorants, perfumes and insect repellents.

* * * * *